US008624061B2

(12) United States Patent
Ceragioli et al.

(10) Patent No.: US 8,624,061 B2
(45) Date of Patent: Jan. 7, 2014

(54) PROCESS FOR THE PREPARATION OF IODINATED CONTRAST AGENT

(75) Inventors: Silvia Ceragioli, Milan (IT); Giovanni Ciarciello, Cesano Maderno (IT); Salvatore Incandela, Barasso (IT); Pietro Minotti, Giussano (IT)

(73) Assignee: Bracco Imaging S.p.A., Milan (IT)

( * ) Notice: Subject to any disclaimer, the term of this patent is extended or adjusted under 35 U.S.C. 154(b) by 76 days.

(21) Appl. No.: 13/127,804

(22) PCT Filed: Nov. 2, 2009

(86) PCT No.: PCT/EP2009/064413
§ 371 (c)(1),
(2), (4) Date: May 5, 2011

(87) PCT Pub. No.: WO2010/057765
PCT Pub. Date: May 27, 2010

(65) Prior Publication Data
US 2011/0207960 A1  Aug. 25, 2011

(30) Foreign Application Priority Data
Nov. 18, 2008 (IT) .............................. MI2008A2042

(51) Int. Cl.
C07C 233/67 (2006.01)
(52) U.S. Cl.
USPC ........................................ 564/142; 564/156
(58) Field of Classification Search
CPC .................................................... C07C 231/02
See application file for complete search history.

(56) References Cited

U.S. PATENT DOCUMENTS 3,835,121 A * 9/1974 Preston .......................... 528/289
4,001,323 A 1/1977 Felder et al.
4,364,921 A 12/1982 Speck et al.
4,822,890 A * 4/1989 Bolin ......................... 548/338.1
5,183,654 A 2/1993 Speck et al.

FOREIGN PATENT DOCUMENTS

| CN | 1302288 A | 7/2001 |
| EA | 005922 B1 | 8/2005 |
| GB | 1472050 A | 4/1977 |
| JP | S5182236 A | 7/1976 |
| JP | H03-173858 A | 7/1991 |
| WO | 98/24757 A1 | 6/1998 |
| WO | 98/54124 A1 | 12/1998 |
| WO | 99/58494 A2 | 11/1999 |
| WO | 99/58494 A3 | 11/1999 |
| WO | 02-44132 A1 | 6/2002 |

OTHER PUBLICATIONS

Haavaldsen J. et al., "X-Ray Contrast Agents. I. Synthesis of Some Derivatives of 5-Amino-2, 4, 6-Triiodoisophthlamide", vol. 20, No. 3, Jan. 1, 1983, pp. 219-232, XP002052827, ISSN: 0001-6675.
PCT International Search Report for PCT/EP2009/064413, mail date Feb. 12, 2010.
PCT Written Opinion of the International Searching Authority for PCT/EP2009/064413, mail date Feb. 12, 2010.
Decision on Grant of Patent for Invention for Russian application No. 2011124888, mail date Apr. 8, 2013.
Office Action for Japanese application No. 2011-536812, mail date Apr. 23, 2013 (English translation).
Office Action for Chinese application No. 200980145584.9, mail date May 31, 2013 (English translation).

* cited by examiner

Primary Examiner — Paul A Zucker
(74) Attorney, Agent, or Firm — M. Caragh Noone

(57) ABSTRACT

The present invention relies on a process for the preparation of non ionic iodinated contrast agents and, in more details, it relates to a process for the preparation of Iopamidol in high yields and with a high degree of purity. In more details, the invention discloses a process for the preparation of a compound of formula (III) comprising the condensation reaction a compound of formula (II) with 2-amino-1,3-propandiol, being said reaction carried out in an aprotic dipolar solvent and in the presence of an alkaline or alkaline rare earth metal oxide or hydroxide.

9 Claims, No Drawings

PROCESS FOR THE PREPARATION OF IODINATED CONTRAST AGENT

CROSS-REFERENCE TO RELATED APPLICATIONS

This application is the national stage application of corresponding international application number PCT/EP2009/064413 filed Nov. 2, 2009, which claims priority to and the benefit of Italian application nos. MI2008A002042, filed Nov. 18, 2008, all of which are hereby incorporated by reference.

FIELD OF THE INVENTION

The present invention generally relates to a process for the preparation of non ionic iodinated contrast agents and, in more details, it relates to a process for the preparation of Iopamidol in high yields and with a high degree of purity. Iopamidol, as well as others non ionic iodinated contrast agents, is employed in the diagnostic field in the X-ray imagine techniques.

BACKGROUND

N,N'-Bis[2-hydroxy-1-(hydroxymethyl)ethyl]-5-[[(2S)-2-hydroxy-1-oxopropyl]-amino]-2,4,6-triiodo-1,3-benzendicarboxamide (see the formula below), generally known as Iopamidol (The Merck Index, XIII Ed., 2001, Nr. 5073), is a compound broadly used for diagnostic methodologies:

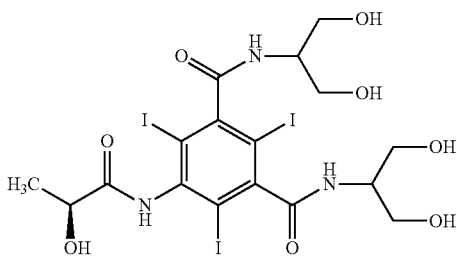 [SMILES: C[C@H](O)C(=O)Nc1c(I)c(C(=O)NC(CO)CO)c(I)c(C(=O)NC(CO)CO)c1I]

Several processes are known in literature for the preparation of Iopamidol, e.g. starting from 5-nitroisophtalic acid, contemplating the use of many reagents and solvent systems, the optional isolation of the synthetic intermediates and the purification of the final product. The 5-nitroisophtalic acid, as a possible starting material, is suitably reduced to the corresponding amine derivative, e.g. by catalytic hydrogenation, and it is subsequently iodinated on the phenyl ring so to form the corresponding 2,4,6-triiodine derivative.

This latter, e.g. in the presence of thionyl chloride, is then converted into the corresponding 5-amino-2,4,6-triiodo-isophthalic acid dichloride, (see, e.g. WO 96/037458, WO96/037459, WO96/016927 and WO96/036590).

The process for the preparation of Iopamidol starting from 5-amino-2,4,6-triiodoisophthalic acid dichloride, comprising possible variations thereof, may be described according to the following synthetic scheme (see, e.g., WO 96/037460, U.S. Pat. No. 5,362,905, WO 97/047590, WO 98/24757, WO 98/028259 and WO 99/058494):

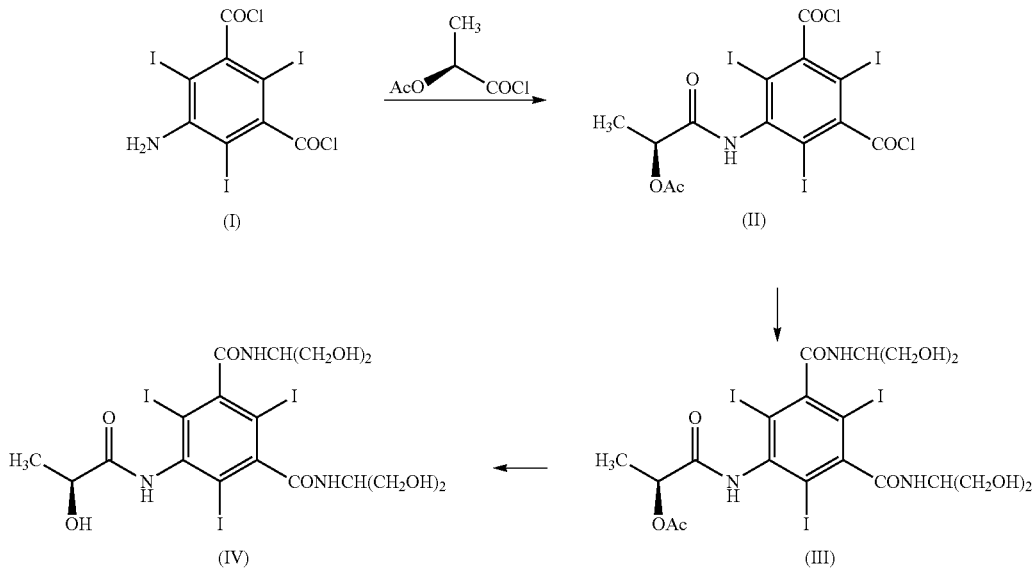

The 5-amino-2,4,6-triiodoisophthalic acid dichloride (I) is converted to the corresponding compound of formula (II) in the presence of (S)-[2-(acetyloxy)]propionic acid chloride. The intermediate of formula (II) thus prepared, is then converted in the acetyl-iopamidol of formula (III) in the presence of 2-amino-1,3-propandiol. Finally, the hydrolysis of the compound of formula (III) and the subsequent purification step, allow for the isolation of Iopamidol (formula (IV).

The use of suitable bases in the condensation reaction between 2-amino-1,3-propandiol and compound (II) is known in the art where, particularly, a tertiary amine is added to the reaction system before the addition of 2-amino-1,3-propandiol (see, e.g., WO 98/24757).

Such addition results to be remarkably advantageous as it enables for the neutralization of the acid being formed during the reaction between compound (II) and 2-amino-1,3-propandiol, avoiding by that, the possible and undesired salification of said acid with the 2-amino-1,3-propandiol.

Among the possible tertiary amines which may be employed, aliphatic tertiary amines, in particular, have been reported, such as, for instance, triethylamine, tripropylamine, tributylamine and diisopropylethylamine.

As disclosed in the aforementioned patent applications, the use of inorganic bases in lieu of the tertiary amines would not result as favourable as the use of a tertiary amine, since it would require particularly long reaction times, due to the insolubility of the bases in the organic reaction solvent, such as e.g. dimethylacetamide (DMA).

Further, the salts resulting from the reaction of the excess of (S)-[2-(acetyloxy)]propionic acid chloride in the reaction system would likely be filtered together with the product, and therefore they might help in compromising the overall yield and the impurities profile of the final product.

To our knowledge, the use of specific bases in the condensation reaction between an aminoalcohol and an appropriate isopthalic acid dichloride, has been described in literature even for the preparation of other non ionic iodinated contrast agents.

We refer, for example, to a process for the preparation of ioversol (The Merck Index, XIII Ed., 2001, Ne. 5085) by reacting 3-amino-1,2-propandiol with 5-acetoxyacetamido-2,4,6-triiodoisopthalic acid dichloride, in the presence of bases and aprotic dipolar organic solvents, particularly dimethylacetamide (DMA) dimethylformamide (DMF) or dimethylsulfoxide (DMSO).

However, the only experimental evidences noticed about the above condensation reaction, whenever said reaction is carried out in the presence of inorganic bases as described, for instance, in the Indian patent IN 187816, contemplate the use of sodium hydroxide in the presence of isopropanol as possible solvent or, alternatively, the employment of potassium carbonate in DMF.

Surprisingly, we have now found that specific inorganic bases, such as, for example, alkaline or rare earth metals oxides or hydroxides, in the reaction conditions as herein set forth, may be conveniently employed in the process for the preparation of iopamidol. Such a process allows at the same time for the neutralization of the acid as formed during the afore mentioned condensation reaction and for the use of mild conditions in the selected solvent. Said process, further, enables for the preparation of iopamidol in high yields and with a high degree of purity.

In this respect, as it is for the others contrast agents being used in the diagnostic field, it is of major importance also for iopamidol that the raw material may be obtained with a high degree of purity so to be able to optimize, even with remarkable results, the purification steps as required for the achievement of the final product, being the latter intended for the administration and therefore in conformity with the limits and the specifications according to Pharmacopoeia.

Among the known impurities related to iopamidol, it is worth noting, in particular, the compound N'-[2-hydroxy-1-(hydroxymethyl)ethyl]-5-[[(2S)-2-hydroxypropanoyl]amino]-2,4,6-triodo-N,N-dimethylbenzene-1,3-dicaroxamide, which structure is reported below:

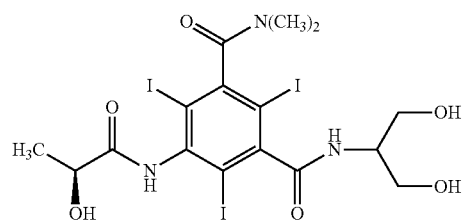 [SMILES: C[C@H](O)C(=O)Nc1c(I)c(C(=O)NC(CO)CO)c(I)c(C(=O)N(C)C)c1I]

The above compound, hereinafter indicated as F-impurity, is within the list of possible side-products generated from the synthesis of iopamidol (e.g. see European Pharmacopoeia 6.0 Ed. 01/2008:1115).

Advantageously, the process of the present invention enables for the preparation of iopamidol with a particularly low amount of F-impurity as well as others side-products, whilst using inorganic bases. All the above allows for the removal of such side products by ordinary purification steps, so to collect the final product within the imposed limitations, as previously indicated

DESCRIPTION OF THE INVENTION

It is, therefore, an object of the present invention, a process for the preparation of a compound of formula (III) comprising the condensation reaction of the acid dichloride of formula (II) with 2-amino-1,3-propandiol, being said reaction carried out in an aprotic dipolar solvent and in the presence of an alkaline or alkaline rare earth metal oxide or hydroxide:

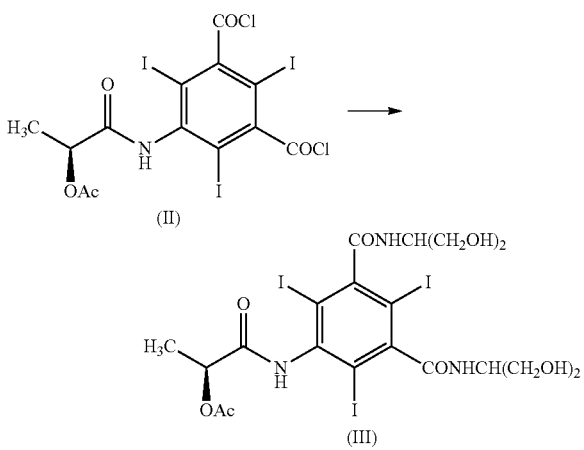

As extensively set forth in the experimental part, the use of such specific inorganic bases enables for the achievement of the product of formula (III) without the drawbacks known in the art.

Unless otherwise provided, the terms "alkaline or alkaline-rare earth metal oxide or hydroxide" mean the lithium, potassium, magnesium or calcium oxides or hydroxides. As regards the oxides, particularly preferred are the calcium and magnesium oxides. Preferably, the reaction is performed in the presence of sodium or calcium hydroxide, and even more preferably, in the presence of calcium hydroxide.

The addition of the hydroxide is carried out according to those techniques conventionally employed in industrial applications, i.e. by adding a suitable amount of the selected base, either in a solid form or as an aqueous solution.

Said addition is performed by a single addition or, alternatively, portion-wise, up to the achievement of the necessary amount of hydroxide.

Typically, the selected base is employed in a ratio of at least 2:1 (equivalents) compared to the amount of compound (II) [i.e. in a ratio of 1:1 (equivalents), compared to the amount of 2-amino-1,3-propandiol] and more preferably in excess.

As reported in the experimental part, the base may be added to the solution of compound (II) either previously, or at the same time, or even after, the addition of 2-amino-1,3-propandiol.

During the addition of the base and 2-amino-1,3-propandiol to the reaction system, the mixture is conveniently stirred, according to the common procedures as industrially employed.

According to a preferred aspect of the invention, the addition of both the 2-amino-1,3-propandiol and the base is performed gradually, by monitoring the reaction mixture temperature, being said temperature kept under about 30° C.

As formerly reported, the reaction is carried out in the presence of an aprotic dipolar organic solvent, preferably dimethylacetamide (DMA).

Both the reactives and the solvents as employed in the reaction are known and broadly used in the industrial context. Also the starting material, i.e. compound of formula (II), is a known compound, and, in case, it can be prepared according to the above scheme, starting from the corresponding 5-amino-2,4,6-triiodoisophthalic acid dichloride of formula (I).

In this respect, it is worth noting that the compound of formula (III) may be obtained according to the process object of the present invention, either starting from compound of formula (II) as such, or, optionally, starting from the corresponding compound of formula (I), without the needing of isolate the intermediate of formula (II), thus formed. Therefore, it is a further object of the present invention a process for the preparation of a compound of formula (III) comprising the steps of:

a) reacting 5-amino-2,4,6-triiodoisophthalic acid dichloride of formula (I) with (S)-[2-(acetyloxy)]propionic acid chloride, in an aprotic dipolar organic solvent, to obtain a solution of the compound of formula (II), and

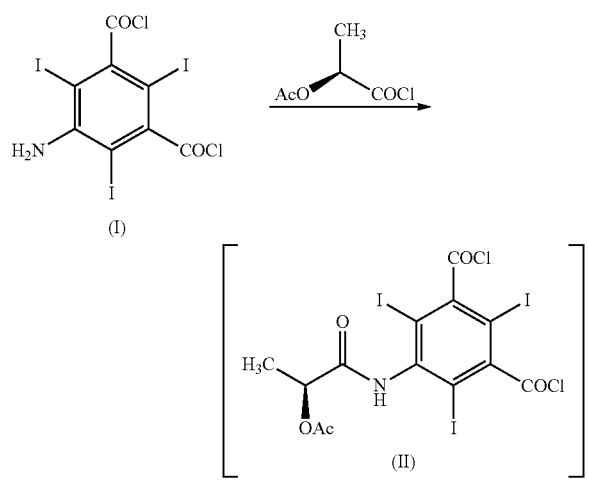

b) adding an alkaline or an alkaline rare-earth metal oxide or hydroxide and 2-amino-1,3-propandiol to the solution of the compound of formula (II), to obtain the compound of formula (III)

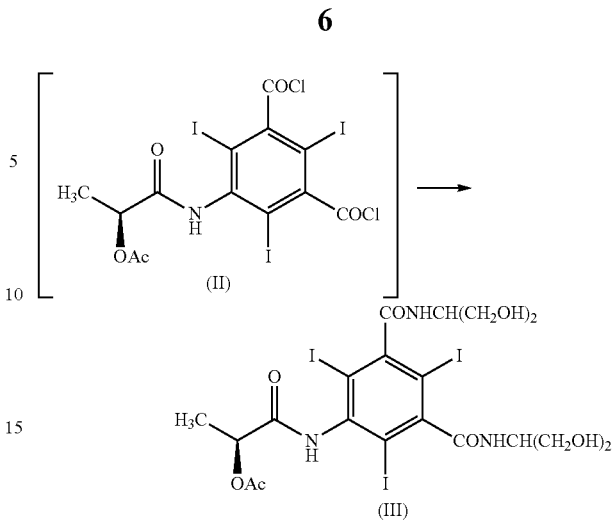

The condensation reaction between the 5-amino-2,4,6-triiodoisophthalic acid dichloride of formula (I) and (S)-[2-(acetyloxy)]propionic acid chloride, as per step (a), is accomplished following methods known in the art, preferably in DMA as possible aprotic dipolar organic solvent.

The thus obtained reaction mixture is then directly added with the selected alkaline or alkaline rare-earth metal oxide or hydroxide along with the suitable amount of 2-amino-1,3-propandiol, in a manner as previously reported.

However, unlike the reaction conducted starting from the isolated derivative of formula (II), in the reaction performed under a procedure "one-pot" the amount of base to be employed is remarkably higher.

In such a case, the base is employed not only for the neutralization of the acid formed during the reaction of amidation between 5-amino-2,4,6-triiodoisophthalic acid dichloride (I) and (S)-[2-(acetyloxy)]propionic acid chloride, but also for the neutralization of the acid that may arise from the possible excess of (S)-[2-(acetyloxy)]propionic acid chloride, and, also, for the neutralization of the acid formed during the amidation reaction between compound (II) and 2-amino-1,3-propandiol. Therefore, according to a preferred embodiment of the invention, when the present process is carried out without isolation of the intermediate (II), the selected base is employed in a ratio of at least 3:1 (equivalents) respect to the amount of 5-amino-2,4,6-triiodoisophthalic acid dichloride of formula (I), and more preferably in excess.

Typically, due to the presence of the acid in the raw reaction material containing the compound of formula (II), the addition of the base to the reaction system is performed before the addition of 2-amino-1,3-propandiol actually occurs.

Also in this case, the addition of the reactives, e.g. the addition of the hydroxide or oxide, either in a solid form or as aqueous solution, and the 2-amino-1,3-propandiol, is preferably effected slowly or portion-wise, under stirring and keeping the temperature below about 30° C.

Even more preferably, the addition of the base to the crude reaction material, which contains the intermediate of formula (II), is conducted at a temperature between about 5° C. and about 20° C.

The thus obtained compound of formula (III), either starting from the isolated compound of formula (II) or starting from the corresponding precursor of formula (I), is afterwards converted in iopamidol (IV), by operating according to the methods known in literature.

Typically, for instance as reported in the experimental part, compound of formula (III) is first isolated from the crude reaction material, purified, optionally by a passage through ionic exchange resins, and then hydrolyzed under basic conditions for the cleavage of the acetyl group.

It is in this respect, a further object of the present invention a process for the preparation of iopamidol (IV) comprising the basic hydrolysis of the corresponding acetyl iopamidol of formula (III), being said compound of formula (III) prepared as previously indicated, i.e. by a condensation reaction of the compound of formula (II), as it is or when present in the crude reaction material, prepared by reaction between 5-amino-2,4,6-triiodoisophthalic acid dichloride of formula (I) and (S)-[2-(acetyloxy)]propionic acid chloride, with 2-amino-1,3-propandiol in an aprotic dipolar solvent and in the presence of an alkaline or rare-earth alkaline metal oxide or hydroxide.

Specific operative conditions and possible variations of the used specifications, e.g. regarding the addition times of the reactives, the optional dilution of the reaction mixture, the excess of the base, the concentration of the selected hydroxide whenever it should be added as aqueous solution or, further possible variations regarding the temperature and/or the reaction time, are to be intended as possible optimization of the process in object and are comprised in the scope of the invention.

The process in object leads to the desired product in high yield and with a high degree of purity. The amount of the existing impurities, and among them the F-impurity as mentioned above, is particularly low so that said impurities may be removed, by conventional purification methodologies.

Moreover, the present process may have a general industrial applicability and may be advantageously applied in the preparation of other iodinated non ionic contrast agents, which synthesis contemplate the condensation reaction between a suitable derivative of the dichloride of the 5-amino-2,4,6-triiodoisophthalic acid and an aminoalcohol. It is therefore an additional object of the present invention a process for the preparation of a compound of formula (VII) comprising the condensation reaction between the acid dichloride of formula (V) with an aminoalcohol of formula (VI), being said reaction carried out in an aprotic dipolar solvent and in the presence of an alkaline or rare-earth alkaline metal oxide or hydroxide

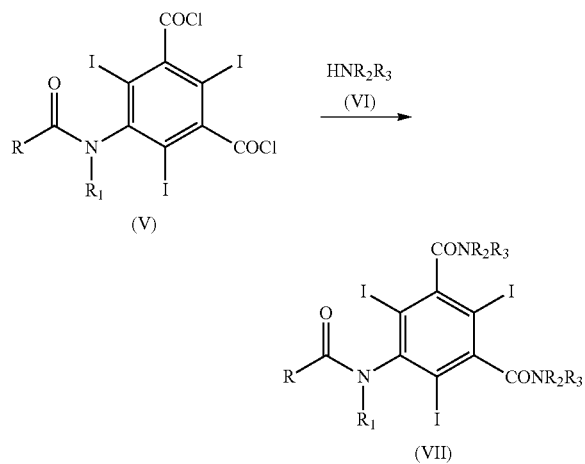

wherein
R is a linear or branched alkyl group with 1 to 6 carbon atoms, optionally substituted by one or more hydroxy groups optionally in a protected form, being said alkyl group optionally interrupted by one or more heteroatoms selected from —O— and —NH—;

$R_1$ is a hydrogen atom or it has one of the meanings of R;

$R_2$ is a linear or branched alkyl group with 1 to 4 carbon atoms, substituted by at least one hydroxy group;

$R_3$ is a hydrogen atom or has one of the meanings of $R_2$.

In the present description, unless otherwise provided, the term "linear or branched alkyl group with 1 to 6 carbon atoms" means those groups such as, for instance, methyl, ethyl, n-propyl, isopropyl, n-butyl, isobutyl, sec-butyl, tert-butyl, n-pentyl, n-hexyl, and the like.

Said alkyl group is optionally substituted by one or more hydroxy groups as such, or preferably, in a protected form.

With the term "protected form" we intend that the hydroxy group is conveniently protected by a suitable moiety which is responsible for the preservation of the subjected group, during the course of the reaction, to be subsequently removed according to known methods, so to cleave the hydroxy group back to the original form.

The hydroxy group is preferably protected by an acyl group, e.g. acetyl (—COCH$_3$), so that the corresponding acetoxy moiety (—OCOCH$_3$) is thus formed.

As a general reference to the use of protecting groups in organic synthesis, see, among others, T. W. Green; Protective Groups in Organic Synthesis (Wiley, N.Y. 1981). Unless stated otherwise, the aminoalcohol of formula (VI) is preferably selected from 2-amino-1,3-propandiol or 3-amino-1,2-propandiol, so that the group $R_2$ corresponds to [—CH(CH$_2$OH)$_2$ or —CH$_2$CHOHCH$_2$OH], respectively.

As regards the aprotic dipolar organic solvent, the proper oxide or hydroxide, as well as the major process parameters, see what previously described.

According to an example of a practical realization, to a solution of 5-amino-2,4,6-triiodoisophthalic acid dichloride (I) in an aprotic dipolar solvent, preferably DMA, is added a suitable amount of (S)-[2-(acetyloxy)]propionic acid chloride, keeping the reaction mixture under stirring at a temperature preferably lower than 30° C.

On completion of the reaction, the reaction mixture is properly diluted with a supplementary amount of solvent and optionally cooled, e.g. at about 15° C.

By subsequent additions under stirring, and keeping the temperature under control, a suitable amount of selected base, for instance powdered calcium hydroxide, along with a proper amount of 2-amino-1,3-propandiol are thus added.

The mixture is finally kept under stirring overnight at the selected temperature, e.g. at about 30° C., up to the completion of the reaction. The obtained raw material is distilled under vacuum to remove the most of the solvent, and the residual crude is diluted with water and purified by means of a cationic resin, according to conventional techniques. The eluted material, containing the product of formula (III), is then hydrolyzed under basic conditions and, at the completion of the reaction, the mixture is adjusted to a pH substantially neutral (i.e. around 7).

The resulting mixture, which contains iopamidol (IV), is finally purified by known methods, comprising, for instance, purification through resins, nano-filtration and crystallization in the presence of a suitable alcohol, such as, e.g., 2-butanol.

The subsequent filtration and drying steps lead to iopamidol (IV) which complies with the afore mentioned purity specifications.

With the intention to better illustrate the present invention and without posing any limits to it, the following examples are accordingly provided.

Example 1

Preparation of the Compound of Formula (III) Starting from the Isolated Compound (II), in the Presence of Calcium Hydroxide Calcium hydroxide (12.8 g, 0.173 mol) was slowly added, under stirring and keeping the temperature below 25° C., to a solution of compound (II) (120 g, 0.169 mol) in 305 g of DMA.

Further on, to the reaction mixture a solution of 2-amino-1,3-propandiol in DMA (133 g, 28% w/w, 0.406 mol) was added dropwise in a period of time of about 45 minutes. The mixture was kept at about 30° C. for 10 hours, up to the completion of the reaction. The crude reaction material containing the derivative of formula (III) may be purified and hydrolyzed according to the procedure of the Example 3 below.
HPLC profile of the mixture after treatment of the sample with NaOH:
Iopamidol (IV): 97.9%;
F-impurity: 0.2%.

Example 2

Preparation of the Compound of Formula (III) Starting from Isolated Compound (II), in the Presence of Sodium Hydroxide Under stirring and keeping the temperature below 25° C., sodium hydroxide (13.9 g, 0.346 mol) was slowly added to a solution of compound (II) (120 g, 0.169 mol) in 305 g of DMA.

Further on, a solution of 2-amino-1,3-propandiol in DMA (133 g, 28% w/w, 0.406 mol) was added dropwise to the reaction mixture, over about 45 minutes. The mixture was maintained at about 30° C. for 10 hours, up to the completion of the reaction.

The crude reaction material containing the derivative of formula (III) may be purified and hydrolyzed according to the procedure of the following Example 3.
HPLC profile of the mixture after treatment of the sample with NaOH:
Iopamidol (IV): 97.4%;
F-impurity: 0.3%.

Example 3

Preparation of Iopamidol (IV) Starting from Isolated Compound (II), in the Presence of Calcium Hydroxide A solution of 2-amino-1,3-propandiol in DMA (610 g, 28% w/w, 1.87 mol) was added to a solution of compound (II) (600 g, 0.845 mol) in DMAC (1510 g) under stirring and over about 45 minutes.

Calcium hydroxide (70.0 g, 0.945 mol) was then slowly added to the reaction mixture keeping the temperature below 30° C. The mixture was further maintained at about 30° C. for 10 hours, until the completion of the reaction.

The crude reaction mixture was then distilled under vacuum (95° C., 10 mbar, 7.5 mmHg) to remove the most of the solvent, up to the obtainment of a viscous residue. The hot residue was then treated with deionised water (1455 g) and the pH was adjusted to 1.7 by addition of hydrochloric acid (33 g, 34% w/w).

The resulting solution was eluted through 1500 mL of a strong cationic exchange resin (Dowex C350™ by DOW) in the Na$^+$ form, to remove the Ca$^{2+}$ ions, along with the excess of 2-amino-1,3-propandiol.

The eluted solution was afterward treated with a solution of sodium hydroxide (250 g, 30%) and kept at about 35° C. for 7 hours, in order to hydrolyse the acetic ester. The pH was then adjusted at a value of about 7 by addition of hydrochloric acid and the resulting solution was treated with sodium sulphite (0.25 g), purified on a PS-DVB resin (1300 mL, Amberlite XAD100™ by Rohm and Haas) and then desalted by nano-filtration.

The final desalting step was performed by a series of two resin plates comprising 425 mL of a strong cationic exchange resin in the H$^+$ form (Dowex C350™) and 500 mL of weak anionic exchange resin (Relite MG1® by Mitsubishi).

The resulting solution was then concentrated under vacuum, obtaining by that a water content of 30% w/w, and the residue was crystallized from 2-butanol (1250 g). The crystallization was completed by adding a suitable aliquot of 2-butanol and by simultaneously distilling off the azeotrope at atmospheric pressure, up to a water content in the suspension close to 3% w/w. After cooling the system at about 25° C., the product was filtered and dried under vacuum at about 50° C., to obtain iopamidol (591 g, 90.0% of yield, starting from compound (II). The thus obtained iopamidol satisfied the purity specifications as required.

Example 4

Preparation of Compound (II)

5-amino-2,4,6-triiodoisophthalic acid dichloride (I) (506 g, 0.85 mol) and dimethylacetamide hydrochloride (37 g) were dissolved in DMA (690 g) at 25° C. To the thus obtained solution, (S)-[2-(acetyloxy)]propionic acid chloride was then added over 4 hours, keeping the temperature between about 10° and 15° C. The temperature of the solution was then set to about 20° C. and stirring was continued for 30 hours. The crude material was used as such, as indicated in the following Examples 5-9.
HPLC profile:
compound (II): 94%;
5-amino-2,4,6-triiodoisophthalic acid dichloride (I): <0.1%.

Example 5

Preparation of the Compound of Formula (III) Starting from the Crude Reaction Material Containing the Compound of Formula (II)

423 g of the crude reaction material in DMA as per Example 4 [0.25 theoretical mol of compound (II)] were diluted with DMA (199 g) and the reaction mixture was cooled at about −5° C. Calcium hydroxide (42 g, 0.567 mol) was then slowly added to the reaction mixture, under stirring and the maintaining the temperature below 5° C.

Subsequently, a solution of 2-amino-1,3-propandiol in DMA was added (231 g, 24% w/w, 0.608 mol) over 1 hour. The mixture was then warmed up to 70° C. and maintained in said conditions for 3 hours, up to the completion of the reaction.
HPLC profile of the mixture, after treatment of the sample with NaOH:
Iopamidol (IV): 89.6%;
F-impurity: 0.4%.

Example 6

Preparation of the Compound of Formula (III) Starting from the Crude Reaction Material Containing the Compound of Formula (II)

The procedure of the Example 5 was modified by operating at a lower temperature, as described herein below.

423 g of the crude reaction material in DMA as per Example 4 [0.25 theoretical moles of compound (II)] were diluted with DMA (200 g) and the mixture was cooled at a temperature of about −5° C. Calcium hydroxide (46.3 g, 0.625 mol) was then slowly added to the reaction mixture, under stirring and at a temperature lower than 5° C. Subsequently, a solution of 2-amino-1,3-propandiol in DMA was added (231 g, 24% w/w, 0.61 mol) over 1 hour. The mixture was then warmed up to about 30° C. and maintained in said conditions for 20 hours, up to the completion of the reaction. HPLC profile of the mixture, after treatment of the sample with NaOH:
Iopamidol (IV): 93.9%;
F-impurity: 0.3%.

Example 7

Preparation of Iopamidol (IV)

1440 g of the crude reaction material in DMA as per Example 4 [(0.85 theoretical mol of compound (II)] were diluted with DMA (677 g) and the reaction mixture was cooled at about 15° C. Calcium hydroxide (157 g, 2.12 mol) was then added to the reaction mixture in 5 portions, under stirring and keeping the temperature below 20° C. After that, a solution of 2-amino-1,3-propandiol in DMA (785 g, 24% w/w, 2.06 mol) was added over one hour. The mixture was then gently heated at 30° C. and kept under such conditions for 20 hours, up to the completion of the reaction. The crude reaction material was then distilled under vacuum (95° C., 10 mbar, 7.5 mmHg) to remove the most of the solvent, until the formation of a viscous residue. The hot residue was hence treated with deionised water (1460 g) and the pH was adjusted to 2 by addition of hydrochloric acid (108 g, 34% w/w).

The resulting solution was then eluted on 2500 mL of a strong cationic exchange resin (Dowex C350™ by Dow) in the Na⁺ form, to remove the Ca⁺⁺ ions along with the excess of 2-amino-1,3-propandiol.

The eluted was then treated with a solution of sodium hydroxide (260 g, 30%) and maintained at 35° C. for 7 hours to hydrolyze the acetic ester. The pH was adjusted to 7 by addition of hydrochloric acid and the resulting solution was treated with sodium sulphite (0.25 g), purified on a PS-DVB resin (1300 mL, Amberlite XAD1600™ by Rohm and Haas) and therefore desalted by nano-filtration. The final desalting step was performed by a series of two resin plates comprising 425 mL of a strong cationic exchange resin in the H⁺ form (Dowex C350™) and 500 mL of a week anionic exchange resin (Relite MG1® by Mitsubishi). The resulting solution was then concentrated under vacuum until the obtainment of a water content of about 30% w/w, and the residue was then crystallized from 2-butanol (1250 g). The crystallization was completed by adding 2-butanol and simultaneously distilling off the azeotrope at atmospheric pressure until the water content in the suspension was about 3% w/w. After cooling at 25° C., the product was filtered and dried under vacuum at about 50° C., to obtain iopamidol (576 g, 87.3% yield starting from compound II). The iopamidol thus obtained satisfies the purity specifications as required.

Comparative Examples

Example 3a

Preparation of Iopamidol (IV) Starting from Isolated Compound (II), in the Presence of Calcium or Magnesium Oxide The same procedure as the previous Example 3 was followed, with the exception that calcium hydroxide was replaced by a same molar amount of either calcium oxide or magnesium oxide. The results are listed below:

| Entry | Base | HPLC Analysis (area %) | |
|---|---|---|---|
| | | Iopamidol | F-impurity |
| 1. | CaO | 98.6 | 0.14 |
| 2. | Ca(OH)$_2$ | 98.5 | 0.14 |
| 3. | MgO | 37.7 | 0.25 |

Example 7a

Preparation of Iopamidol (IV) in the Presence of Calcium Oxide

The same procedure as the previous Example 7 was followed, with the exception that calcium hydroxide was replaced by a same molar amount of calcium oxide.

Iopamidol was obtained with 83.0% yield starting from compound II and satisfies the purity specifications as required.

Example 8

Preparation of the Compound of Formula (III) in the Presence of Sodium Carbonate The same procedure as the previous Example 5 was modified by using sodium carbonate in place of calcium hydroxide, as follow.

423 g of the crude reaction material in DMA as per Example 4 (0.25 theoretical mol of compound II) was diluted with DMA (200 g) and the mixture was cooled at −5° C. Sodium carbonate (119 g, 1.13 mol) was then slowly added to the reaction mixture, under stirring and keeping it at a temperature lower than 5° C. Afterwards, a solution of 2-amino-1,3-propandiol in DMA (231 g, 24% w/w, 0.61 mol) was added over 1 hour. The mixture was then heated at 70° C. and maintained in such conditions for 3 hours until the completion of the reaction.
HPLC profile:
iopamidol (IV): 92.0%
F-impurity: 0.2%
Total impurities: 8%.

After filtration of the salts, operating as per Example 3, iopamidol (IV) was obtained (yield=78.0%) by purification and hydrolysis of the compound of formula (III). The product does not satisfy the purity specifications.

Example 9

Comparative Example for the Preparation of Compound of Formula (III) in the Presence of Triethylamine The procedure as per Example 5 was modified by using trietilamine in place of calcium hydroxide as follow.

423 g of the crude reaction material in DMA as per Example 4 (0.25 theoretical mol of compound II) was diluted with DMA (199 g) and the mixture was cooled at a temperature of about −5° C. Triethylamine (114 g, 1.13 mol) was then slowly added to the reaction mixture, under stirring and keeping the temperature lower than 5° C. After that, a solution of 2-amino-1,3-propandiol in DMA (231 g, 24% w/w, 0.61 mol) was added over 1 hour. The mixture was then heated at 70° C. and maintained in such conditions for 3 hours until the completion of the reaction.

By operating in an analogue manner as Example 3, iopamidol (IV) was thus obtained by purification and hydrolysis of the compound of formula (III).
HPLC profile:
iopamidol (IV): 89.1%;
F-impurity: not detected;
Total impurities: 10.9%.

The invention claimed is:

1. A process for the preparation of a compound of formula (VII) comprising the condensation reaction between a compound of formula (V) and the aminoalcohol of formula (VI), said reaction being carried out in an aprotic dipolar organic solvent and in the presence of an alkaline or alkaline rare-earth metal oxide or hydroxide

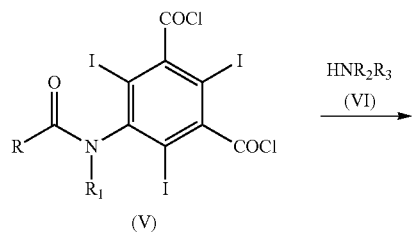

(V)

HNR$_2$R$_3$
(VI)

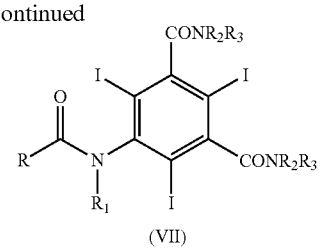

(VII)

wherein:
R is a linear or branched alkyl group with 1 to 6 carbon atoms, optionally substituted by one or more hydroxy group optionally in a protected form, said alkyl group optionally interrupted by one or more heteroatoms selected from —O— and —NH—;
R$_1$ is a hydrogen atom or R;
R$_2$ is a linear or branched alkyl group with 1 to 4 carbon atoms, substituted by at least one hydroxy group;
R$_3$ is a hydrogen atom or R$_2$.

2. A process according to claim 1, wherein the alkaline or alkaline rare-earth metal hydroxide is selected from sodium and calcium hydroxide.

3. A process according to claim 2, wherein the hydroxide is calcium hydroxide.

4. A process according to claim 1, wherein the alkaline or alkaline rare-earth metal oxide is selected from magnesium and calcium oxide.

5. A process according to claim 1, wherein the aprotic dipolar organic solvent is dimethylacetamide (DMA).

6. A process according to claim 5 wherein the solvent is DMA and the hydroxide is selected from sodium and calcium hydroxide.

7. A process according to any one of claim 1, 2 or 4 wherein:
R is —CH(OCOCH$_3$)CH$_3$;
R1 is H;
R2 is —CH(CH$_2$OH)$_2$, and
R3 is H.

8. A process according to claim 1 wherein the compound of formula (V) wherein R$_1$ is H and R is CH(OCOCH$_3$)CH$_3$, is obtained by reacting 5-amino-2,4,6-triiodoisophthalic acid dichloride of formula (I) with (S)-[2-(acetyloxy)]propionic acid chloride, in an aprotic dipolar organic solvent.

9. A process according to claim 1 which further comprises the step of submitting compound (VII) to a basic hydrolysis, to obtain iopamidol (IV).

* * * * *